United States Patent
Jeong et al.

(10) Patent No.: US 11,291,399 B2
(45) Date of Patent: Apr. 5, 2022

(54) APPARATUS FOR MEASURING ELECTROCARDIOGRAM, AND METHOD OF OPERATION THE APPARATUS

(71) Applicant: ATSENS CO., LTD., Gyeonggi-do (KR)

(72) Inventors: Jong Ook Jeong, Gyeonggi-do (KR); Chang Ho Lee, Gyeonggi-do (KR); Bang Won Lee, Gyeonggi-do (KR)

(73) Assignee: ATSENS CO., LTD., Gyeonggi-do (KR)

( * ) Notice: Subject to any disclaimer, the term of this patent is extended or adjusted under 35 U.S.C. 154(b) by 0 days.

(21) Appl. No.: 16/998,418

(22) Filed: Aug. 20, 2020

(65) Prior Publication Data
US 2022/0054035 A1   Feb. 24, 2022

(51) Int. Cl.
*A61B 5/349* (2021.01)
*A61B 5/00* (2006.01)
*A61B 5/316* (2021.01)

(52) U.S. Cl.
CPC .......... *A61B 5/349* (2021.01); *A61B 5/316* (2021.01); *A61B 5/7225* (2013.01); *A61B 5/6833* (2013.01)

(58) Field of Classification Search
CPC ....... A61B 5/349; A61B 5/316; A61B 5/7225; A61B 5/6833
See application file for complete search history.

(56) References Cited

U.S. PATENT DOCUMENTS

| | | | |
|---|---|---|---|
| 2019/0015006 A1* | 1/2019 | Chen | A61B 5/725 |
| 2019/0336026 A1* | 11/2019 | Dawoud | A61B 5/283 |

FOREIGN PATENT DOCUMENTS

| | | |
|---|---|---|
| JP | H01198532 | 8/1989 |
| JP | 2002306437 | 10/2002 |
| KR | 1020060117545 | 11/2006 |
| KR | 101410989 | 6/2014 |
| WO | 140107017 | 7/2014 |

OTHER PUBLICATIONS

Office Action dated Aug. 21, 2020 for the corresponding KR Application No. 10-2019-0031471 and English translation (total 20 pages).

\* cited by examiner

*Primary Examiner* — Catherine M Voorhees
*Assistant Examiner* — Roland Dinga
(74) *Attorney, Agent, or Firm* — Burris Law, PLLC

(57) ABSTRACT

An apparatus for measuring an electrocardiogram includes a signal detector, a signal converter, and a processor. The apparatus detects a particular component from an electrocardiogram digital signal and generates measurement data for an electrocardiogram digital signal by applying different conversion gains to an interval including the particular component and a remaining interval.

14 Claims, 13 Drawing Sheets

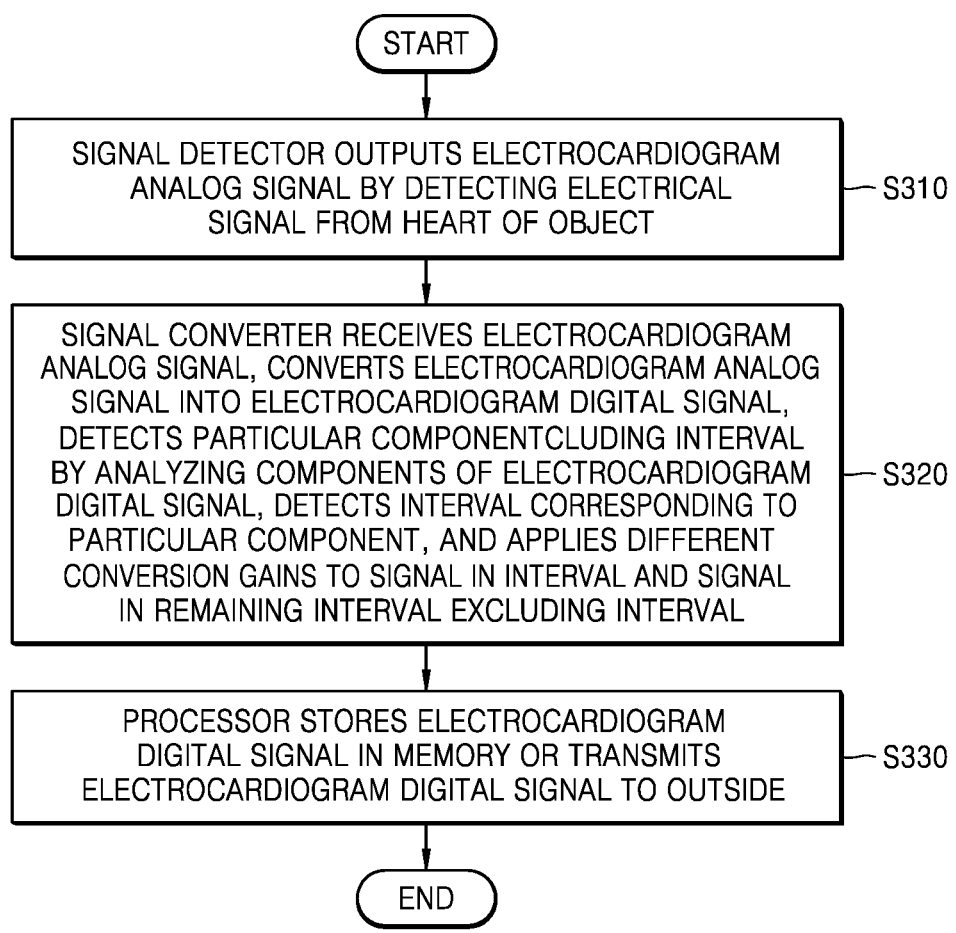

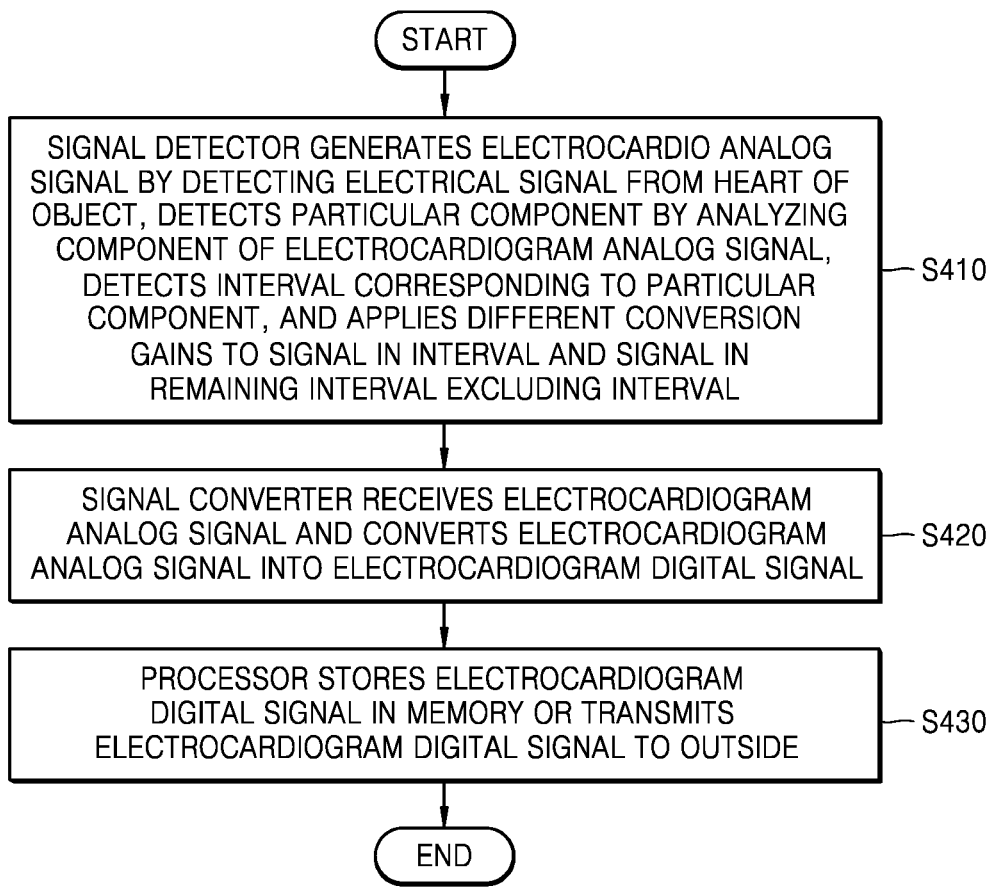

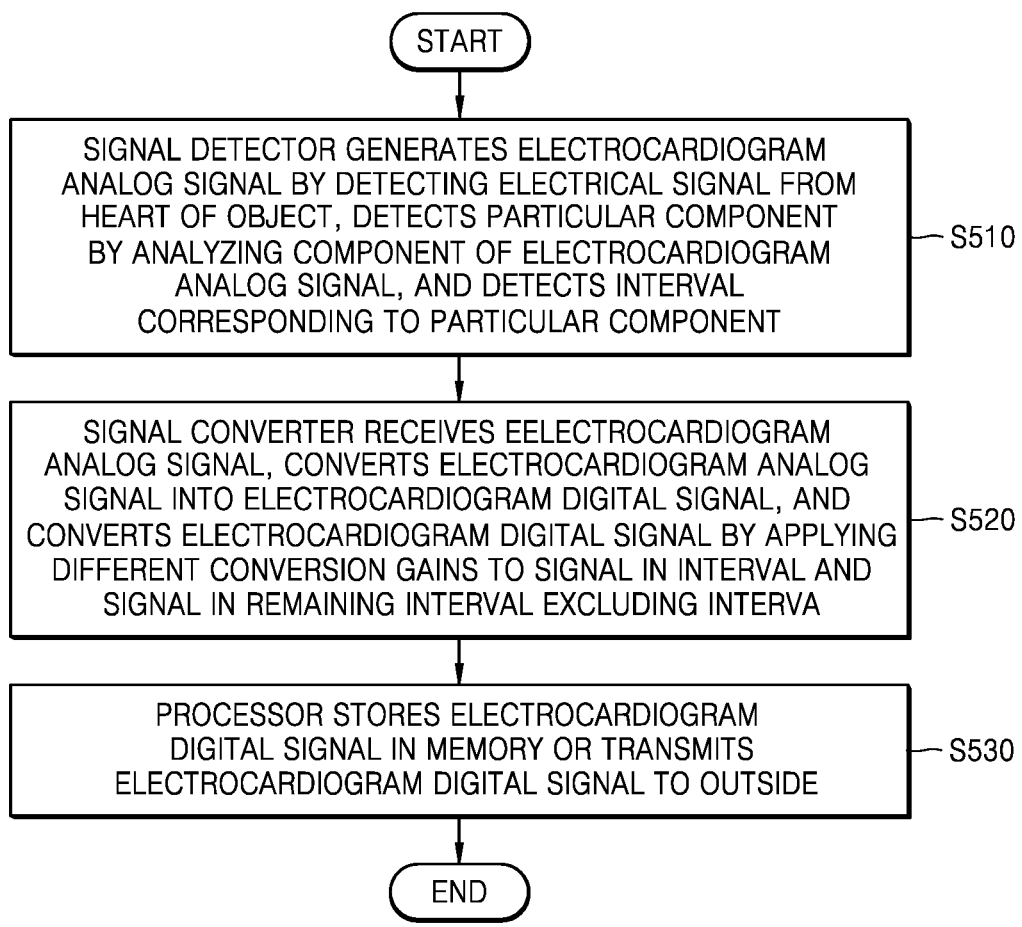

APPARATUS FOR MEASURING ELECTROCARDIOGRAM, AND METHOD OF OPERATION THE APPARATUS

FIELD

One or more embodiments relate to an apparatus for measuring an electrocardiogram and a method of operation of the apparatus.

BACKGROUND

In order to maintain human life, there is a need for a process of enabling blood released by the heartbeat to flow along the arteries to all parts of the body without clogging and returning blood through the veins back to the heart. Accordingly, oxygen and nutrients may be supplied to the body's tissues, and consumed wastes may be removed through the metabolism.

However, when the human heart is in a poor condition, blood may not be properly delivered to particular parts of the body or a blood clot or embolism may occur in the blood. As a result, blood may become cloudy, and the cloudy blood may block capillaries, in particular tissues of the body, and cause tissue necrosis, and thus, the human life may be in danger. Therefore, in addition to clinical examinations, imaging tests and the like have been used to examine whether or not the heart is abnormal. Also, as an early diagnosis method, a method of determining whether or not a patient has an abnormality in the heart by measuring an electrocardiogram and displaying the measured electrocardiogram signal in a graph format has also been widely used.

In other words, an electrocardiogram refers to recording of a potential change in the surface of the body causing the mechanical activity of the heartbeat, such as contraction or expansion of the heart muscle. The electrocardiogram is a non-vascular test that is simply measured, is easily reproduced, is easily repetitively recorded, and is inexpensive to test. The electrocardiogram has been used helpfully to diagnose arrhythmia and coronary artery disease (cardiac artery disease) and to monitor the progress of cardiac patients.

In general, the sensing electrodes of the electrocardiogram are attached to the upper left and right and lower left and right of the chest. And potential differences are detected according to the location of the sensor.

An apparatus for measuring an electrocardiogram refers to an apparatus which records and displays a variation curve (a frequency component of about 0.1 Hz to about 200 Hz) in time and a minute potential difference (voltage of 1 mV) when the heart beats. The curve obtained at this time is referred to as an electrocardiogram.

SUMMARY

One or more embodiments include an apparatus for measuring an electrocardiogram, for enhancing a small-sized signal (e.g., P-wave component) of an electrocardiogram.

The technical problems to be solved by the present embodiment are not limited to the technical problems as described above, and other technical problems may be inferred from the following embodiments.

Additional aspects will be set forth in part in the description which follows and, in part, will be apparent from the description, or may be learned by practice of the presented embodiments of the disclosure.

A computer program according to one or more embodiments may be stored on a medium to execute, by using a computer, any one of methods according to one or more methods.

In addition, provided are other methods, other systems, and computer-readable recording media recording thereon a computer program for executing the method.

Other aspects, features, and advantages than those described above will become apparent from the following drawings, claims, and detailed description.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 9 is a flowchart of a method of measuring an electrocardiogram, according to another embodiment;

FIG. 10 is a flowchart of a method of measuring an electrocardiogram, according to further another embodiment; and FIG. 11 is a flowchart of a method of measuring an electrocardiogram, according to yet further another embodiment.

DETAILED DESCRIPTION

Figure 1A:
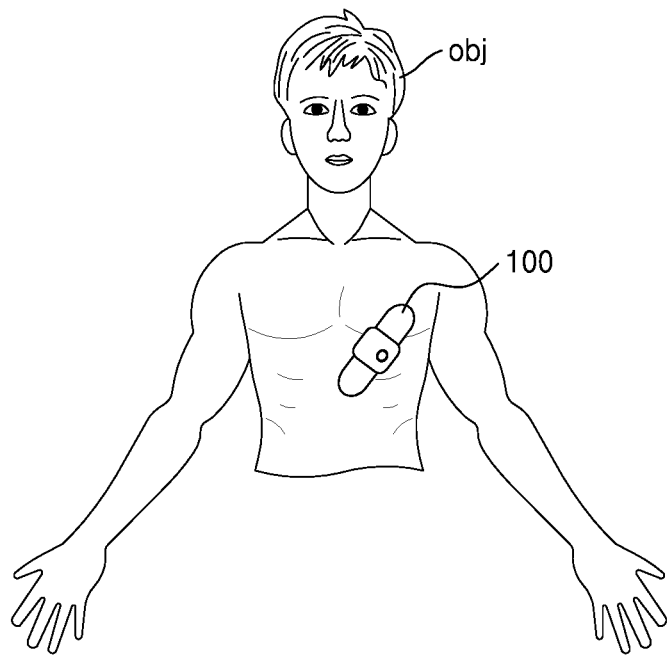
FIG. 1A is a view of an embodiment of an apparatus for measuring an electrocardiogram, according to one or more embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

With respect to the terms in the various embodiments, the general terms which are currently and widely used are selected in consideration of functions of structural elements in the various embodiments of the present disclosure. However, meanings of the terms can be changed according to intention, a judicial precedence, the appearance of a new technology, and the like. In addition, in certain cases, a term which is not commonly used can be selected. In such a case, the meaning of the term will be described in detail at the corresponding portion in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er," "-or," and "module" described in the specification mean units for processing at least one function and operation and can be implemented by hardware components or software components and combinations thereof.

Hereinafter, the present disclosure will now be described more fully with reference to the accompanying drawings, in which exemplary embodiments of the present disclosure are shown such that one of ordinary skill in the art may easily work the present disclosure. The disclosure may, however, be embodied in many different forms and should not be construed as being limited to the embodiments set forth herein.

Hereinafter, one or more embodiments will be described in detail with reference to the accompanying drawings.

Atrial fibrillation is one of the most common kinds of arrhythmia clinically, and an overall prevalence thereof is about 0.4% to 0.9%. From the age of 40 onwards, the prevalence of atrial fibrillation increases by about 0.1% to about 0.2% each year and increases to about 2% to about 4% when the age is 60 years or older. When atrial fibrillation is accompanied, atrial-to-ventricular synchronization is lost and ventricular diastolic is shortened, thereby causing respiratory difficulty and cardiac failure. Also, in patients with atrial fibrillation, a thrombus is created in the atrium and causes a systemic embolism such as cerebral infarction, thereby increasing a mortality rate. The increase in the occurrence of atrial fibrillation along with the increase in the aged population has significant health and sociological meanings in this regard. Because paroxysmal atrial fibrillation may develop into chronic atrial fibrillation, the prediction and diagnosis of the occurrence risk of paroxysmal atrial fibrillation are significant.

Among ECG signal components, a P-wave component has been used as significant information for predicting and diagnosing such atrial fibrillation. Therefore, it is highly significant to develop electrocardiogram measuring apparatuses capable of generating ECG signals in which P-wave components are well expressed.

In particular, recently, large hospitals have used expensive ultrasonic medical devices to accurately observe the heart conditions, and thus, the utilization of electrocardiogram measuring apparatuses has gradually decreased. However, P-wave components may not be measured even through ultrasonic medical devices provided in large hospitals or the like.

According to one or more embodiments, a P-wave component from among ECG signal components may be further enhanced in a process of generating an input analog ECG signal. A P-wave component may be enhanced by applying different conversion gains to a signal in a PR interval and a signal in the remaining interval.

According to one or more embodiments, signal gain may be an element for adjusting the magnitude of an electrocardiogram signal in a process of converting an electrocardiogram analog signal into an electrocardiogram digital signal. For example, the gain of a PR interval may be 0×66, and the gain of the remaining interval may be 0×33. Note that 0×66 and 0×33 are hexadecimal numbers that determines signal gain. As the gain of the PR interval is greater than that of the remaining interval, the magnitude of a P-wave component may be increased. Therefore, the magnitude of a particular component such as a P-wave component of an electrocardiogram signal may be increased, and the particular component may be visually easily detected.

In one or more embodiments, when the gain is set to be constantly high in the entire interval of an electrocardiogram (ECG) signal, signal stability caused by various types of noise, such as body noise and noise due to motions, may be lowered.

FIG. 1A is a view of a network environment of an apparatus for measuring an electrocardiogram, according to one or more embodiments.

As illustrated in FIG. 1A, an apparatus 100 for measuring an electrocardiogram (hereinafter referred to as the electrocardiogram measuring apparatus 100) is an apparatus which is mounted on an object obj noninvasively or invasively to detect an electrocardiogram according to the heartbeat of the object obj. Here, the object obj may be a human, an animal, or part of the body of a human or animal such as the chest but is not limited thereto. The object obj may include all types of objects from which electrocardiograms may be detected or measured. Also, an electrocardiogram is a graph that records changes in a potential appearing on the surface of the body according to the mechanical activity of the heartbeat such as contraction/expansion of the myocardium. Here, the meaning "detect an electrocardiogram" may be the same as the meaning "detect a potential" occurring on the surface of the body according to the heartbeat of an object. An apparatus for measuring an electrocardiogram may transmit and receive data with a user terminal by using a communication module. The communication module may include various types of communication modules such as a wireless Internet module, a near field communication module, and a mobile communication module.

The wireless Internet module refers to a module that is connected to an external network to perform communication according to communication protocols such as wireless LAN (WLAN), Wi-Fi, wireless broadband (Wibro), world interoperability for microwave access (Wimax), and high speed downlink packet access (HSDPA).

The near field communication module refers to a module for performing communication with an external device located at a short distance, according to near field communication methods such as Bluetooth, radio frequency identification (RFID), infrared data association (IrDA), ultra wideband (UWB), and ZigBee.

The mobile communication module refers to a module that accesses a mobile communication network to perform communication according to various types of mobile communication standards such as $3^{rd}$ generation (3G), $3^{rd}$ generation partnership project (3GPP), and long term evolution (LTE).

However, the communication module is not limited thereto and may also apply other types of communication modules capable of performing communication with the electrocardiogram measuring apparatus 100 and transmitting and receiving various types of signals and data, in addition to those described above.

The electrocardiogram measuring apparatus 100 may further include a band-type or gel-type mounting part. The mounting part may be made of a flexible material that may be deformed to fit a curved surface of the surface of the body, for example, an elastic, i.e., flexible fabric. The mounting part may be provided as a patch-type or wearable type of a tape-type or gel-type. As long as the electrocardiogram measuring apparatus 100 is worn through the mounting part, the electrocardiogram measuring apparatus 100 may detect a potential generated on the surface of the body by contacting the surface of the body of the object obj.

Figure 1B:
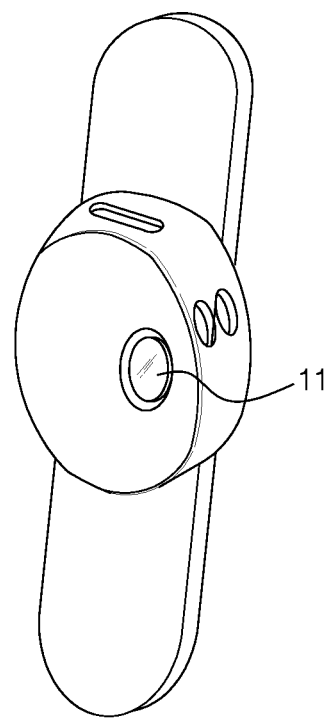
FIG. 1B is a perspective view of an apparatus for measuring an electrocardiogram.

As illustrated in FIG. 1B, the electrocardiogram measuring apparatus 100 may include a button 11. The electrocardiogram measuring apparatus 100 may input preset on/off through the button 11. The electrocardiogram measuring apparatus 100 has an outer appearance covered with cases 21 and 22. The cases 21 and 22 may form the outer appearance of the electrocardiogram measuring apparatus 100 and may accommodate and protect various elements in a space formed therein.

The cases 21 and 22 may be made of a plastic material that does not transfer heat or a metal material that is coated with a heat barrier material on the surface thereof. The cases 21 and 22 may be manufactured by, for example, an injection molding method, a 3D printing method, or a method of assembling small parts manufactured by injection molding.

Figure 1C:
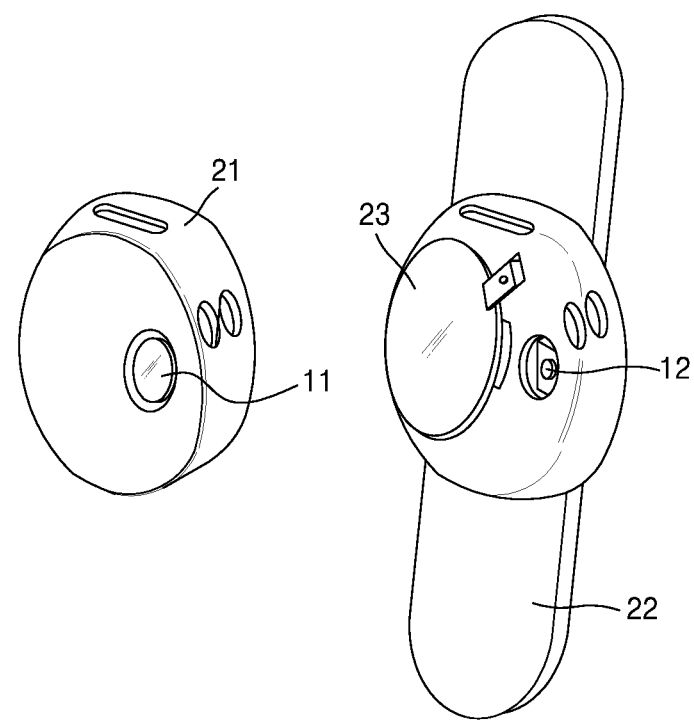
FIG. 1C is a side view of the apparatus for measuring an electrocardiogram of FIG. 1B.

In the electrocardiogram measuring apparatus 100 according to the embodiment illustrated in FIGS. 1B and 1C, the cases 21 and 22 are not vital elements and may not be installed as needed.

The button 11 may be arranged on the top of the case 21 and receive an input from a user.

As illustrated in FIG. 1C, when the case 21 of the electrocardiogram measuring apparatus 100 is removed, a battery 23 for supplying power and a button 12 are exposed. When the case 21 is removed, elements corresponding to a signal detector 110, a signal converter 120, a signal processing unit 125, a processor 130, a sensor unit 140, a memory 160, and a communicator 170 for operation of the electrocardiogram measuring apparatus 100 may be exposed.

Figure 2:
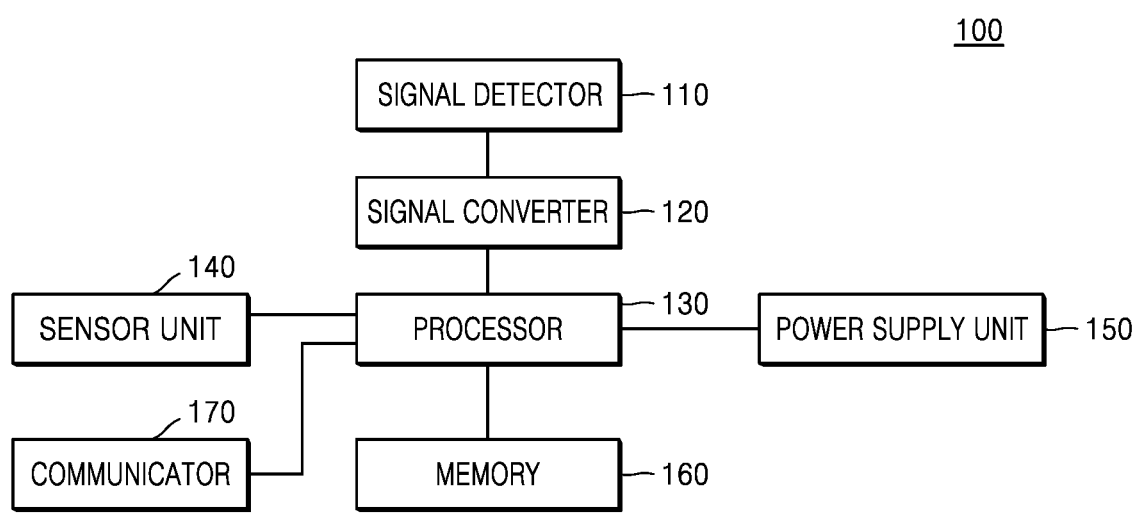
FIG. 2 is a block diagram of an apparatus for measuring an electrocardiogram according to one or more embodiments.

FIG. 2 is a block diagram of an apparatus for measuring an electrocardiogram according to one or more embodiments.

As illustrated in FIG. 2, an apparatus 100 for measuring an electrocardiogram (hereinafter referred to as the electrocardiogram measuring apparatus 100) may include the signal detector 110, the signal converter 120, the signal processing unit 125, the processor 130, the sensor unit 140, the power supply unit 150, the memory 160, and the communicator 170 to detect an electrical signal generated from the heart of an object. Note that the signal processing unit 125 is not drawn in FIG. 2 because the signal processing unit 125 is usually implemented in firmware of the processor 130.

The signal detector 110 outputs an electrocardiogram analog signal by detecting an electrical signal from the heart of the object.

The signal converter 120 may convert the electrocardiogram analog signal into an electrocardiogram digital signal. The processor 130 receives the electrocardiogram digital signal and records the electrocardiogram digital signal in the memory 160.

The signal processing unit 125 may detect a particular component, for example, a P-wave component by analyzing components of the electrocardiogram digital signal or the electrocardiogram analog signal, detect a first interval corresponding to the particular component, apply different conversion gains to a signal in the first interval and a signal in a remaining second interval excluding the first interval, and generate measurement data of an electrocardiogram signal to which a conversion gain is applied. The processor 130 may record the electrocardiogram digital signal or the measurement data of the electrocardiogram signal in the memory 160. Also, the processor 130 may transmit, to an external electronic device, the electrocardiogram digital signal or the measurement data of the electrocardiogram signal.

The signal processing unit 125 may detect the particular component from the electrocardiogram digital signal by using the magnitude and slope of a signal. The signal processing unit 125 may detect an average magnitude or an average slope of the particular component on the basis of data about collected particular components and detect the particular component through the data about the collected particular components. The signal processing 125 may collect data about particular components for each object. For example, data about a particular component may be collected separately, such as data about a particular component of a first object and data about a particular component of a second object. The collected data about the particular components may be recorded in the memory 160. The collected data about the particular components may be acquired from an external electronic device. Here, a particular component may be related to cardiac movement and may be a P wave, an R wave, or the like.

In another embodiment, the signal processing unit 125 may detect a particular component by comparing an electrocardiogram digital signal with a template of a standard electrocardiogram waveform.

In another embodiment, the signal processing unit 125 may detect a peak component from an electrocardiogram signal by using the magnitude and slope of a signal and detect a P-wave component by using the peak component. The peak component may refer to a component including a point at which the magnitude of a signal is largest within an interval of the electrocardiogram signal. The interval may be appointed by the heart movement of an object. The signal processing unit 125 may detect a P-wave component occurring closest to the peak component, in an interval preceding the peak component. "The closest occurrence of the P-wave component" means that the P-wave component occurs first in an interval preceding or following the peak component, and second and third occurrences of the P-wave component, and the like are excluded. A P-wave component is a point that shows a diphasic pattern in order of a peak and a valley of a signal and is a component that is detected during atrial contraction.

In relation to the detection of the peak component, the signal processing unit 125 may detect, as the peak component, a time point at which a slope value of a signal is changed from a positive value to a negative value, i.e., a time point at which the slope value of the signal is 0 or infinite, a time point at which the magnitude of the signal reaches a maximum value, or the like. The signal processing unit 125 may detect, as a particular component, an interval in which a time length and/or magnitude of a signal is within a preset range, from an interval preceding the peak component. The signal processing unit 125 may detect, as a particular component, an interval which occurs closest to the peak component and at which the magnitude of a signal is not 0, from an interval before the peak component. The signal processing unit 125 may detect, as a P-wave component, an interval which occurs closest to the peak component and at which a shape of an electrocardiogram signal is similar to a preset template signal, from an interval before a peak component.

The signal processing unit 125 may generate measurement data for an electrocardiogram signal by applying a first conversion gain to a signal in a first interval and applying a second conversion gain to a signal in a remaining interval excluding the first interval. Here, the second conversion gain may be a value different from the first conversion gain and may be a value less than the first conversion gain. Therefore, the electrocardiogram measuring apparatus 100 may enhance detection, visual display, recognition, and the like of a particular component by applying, to an interval including a particular component, a conversion gain greater than a conversion gain applied to a remaining interval.

The signal processing unit 125 may detect, as a particular component, an interval in which a slope value or an absolute value of the slope value is less than or equal to a preset value and the magnitude of a signal is not 0, from an interval before a peak component. The signal processing unit 125 may set an interval on the basis of a particular component detected as described above.

The signal processing unit 125 detects a peak component, determines a first interval including a P-wave component on the basis of the detected peak component, and determines a first interval and a remaining second interval excluding the first interval. The processor 130 may apply different conversion gains to the first interval and the second interval, respectively.

The signal processing unit 125 may detect a peak component including a point at which the magnitude of a signal is a maximum value and set an interval including a particular component on the basis of an interval including the peak component. The signal processing unit 125 may set, to an interval including a particular component, a set of points which are adjacent to a peak component and at which a slope is not 0.

Before applying a conversion gain, the signal processing unit 125 may entirely amplify the magnitude of an electrocardiogram signal by applying a preset initial conversion gain to components of the electrocardiogram signal.

The processor 130 may control conversion gain but is not limited thereto, and the signal converter 120 may control the magnitude of conversion gain.

The processor 130 may control operation of the signal detector 110, the signal converter 120, or the signal processing unit 125, but the signal detector 110, the signal converter 120, or the signal processing unit 125 may operate autonomously. The processor 130 may also be controlled autonomously. Here, the signal processing unit 125 is implemented in hardware. But it is natural that the signal processing unit 125 can be realized in firmware of the processor 130.

The signal processing unit 125 may apply a conversion gain to an interval including a P-wave component that is a particular component and apply a conversion gain of 0 to a remaining interval excluding the interval including the P-wave component. Conversion gain may be applied to the magnitude of a signal by addition or multiplication, and thus, the electrocardiogram measuring apparatus 100 may significantly reduce the capacity of measurement data of an electrocardiogram signal. The processor 130 may store, in the memory 160, a conversion gain or a conversion control signal along with an electrocardiogram signal to which the conversion gain is applied. The processor 130 may transmit, to an external user terminal or a remote storage device, a conversion gain or a conversion control signal along with an electrocardiogram signal in a wired/wireless communication method (e.g., through a near field communication network).

The processor 130 may store, in the memory 160, measurement data of the electrocardiogram signal to which the conversion gain is applied.

In an alternative embodiment, the processor 130 may further include a module for generating measurement data on the basis of an electrocardiogram digital signal. The module for generating measurement data may detect a particular component, for example, a P-wave component, by analyzing components of an electrocardiogram digital signal or an electrocardiogram analog signal, detect a first interval corresponding to the particular component, apply different conversion gains to a signal in the first interval and a signal in a remaining second interval excluding the first interval, respectively, and generate an electrocardiogram digital signal to which the conversion gain is applied.

The module for generating measurement data may detect a particular component from an electrocardiogram digital signal by using the magnitude and slope of a signal. An average magnitude or an average slope of a particular component may be detected on the basis of collected data about P-wave components, and a particular component may be detected through the collected data about the P-wave components. The data about the P-wave components may be collected separately for each object. When there is no history of data collected for P-wave components of an object to be measured, data about P-wave components that are not limited to the object may be collected.

In another embodiment, the module for generating measurement data may detect a particular component by analyzing an electrocardiogram digital signal with a template of a standard electrocardiogram waveform.

In another embodiment, the module for generating measurement data may detect a peak component from an electrocardiogram signal by using the magnitude and slope of a signal and detect a P-wave component by using the peak component. Here, the peak component may refer to a component including a point at which the magnitude of a signal is within an interval of an electrocardiogram signal. The interval may be appointed by cardiac movement of an object. The module for generating measurement data may detect, as a P-wave component, a component at which the magnitude of a signal generated closest to a peak component is not 0, from an interval preceding the peak component.

In relation to detection of a peak component, the module for generating measurement data may detect, as a peak component, a time point at which a slope value of a signal is changed from a positive (+) value to a negative (−) value, i.e., the slope value of the signal is 0 or is infinite, a time point at which the magnitude of the signal reaches a maximum value, or the like. The module for generating measurement data may detect, as a particular component, an interval in which a time length and/or magnitude of a signal is within a preset range, from an interval before a peak component. The module for generating measurement data may detect, as a particular component, an interval in which the magnitude of a signal generated closest to a peak component is not 0, from an interval before the peak component. The module for generating measurement data may detect, as a P-wave component, an interval which occurs closest to a peak component and in which a shape of an electrocardiogram signal is similar to a preset template, from an interval before the peak component.

The module for generating measurement data may generate measurement data for an electrocardiogram signal by applying a first conversion gain to a signal in a first interval including a particular component and applying a second conversion gain to a signal in a remaining interval excluding the first interval. Here, the second conversion gain may be a value different from the first conversion gain and may be a value less than the first conversion gain. As a result, the electrocardiogram measuring apparatus 100 may enhance detection, visual display, recognition, and the like of a particular component by applying, to an interval including a particular component, a conversion gain greater than a conversion gain applied to a remaining interval.

Alternatively, the module for generating measurement data may detect, as a particular component, an interval in which a slope value of a signal or an absolute value of the slope value is less than or equal to a preset value and the magnitude of the signal is not 0, from an interval before a peak component. The module for generating measurement data may set an interval on the basis of a particular component detected as described above.

Alternatively, the module for generating measurement data detects a peak component, determines a first interval including a P-wave component on the basis of the detected peak component, and determines a first interval and a second interval excluding the first interval. The module for generating measurement data may apply different conversion gains to the first interval and the second interval, respectively.

Alternatively, the module for generating measurement data may detect a peak component including a point at which the magnitude of a signal is a maximum value and set an interval including a particular component on the basis of an interval including the peak component. The module for generating measurement data may set, as an interval including a peak component, a set of points which are adjacent to the peak component and at which a slope is not 0.

Alternatively, before applying a conversion gain, the module for generating measurement data may entirely amplify the magnitude of an electrocardiogram signal by applying a preset initial conversion gain to the electrocardiogram signal.

Alternatively, the module for generating measurement data may apply a conversion gain to an interval including a P-wave component and apply a conversion gain of 0 to an interval excluding the interval including the P-wave component.

The module for generating measurement data may be implemented with software or hardware, and part of the module for generating measurement data may be implemented with software, and the other part of the module for generating measurement data may be implemented with hardware.

Alternatively, the processor 130 may store, in the memory 160, additional event information along with an electrocardiogram signal. When an abnormal event is detected from an electrocardiogram digital signal, the processor 130 may detect a time point at which the abnormal event is detected and a corresponding interval of measurement data, insert, into the measurement data, a tag related to an event in association with the interval of the measurement data, and transmit, to an external user terminal, the measurement data into which the tag is inserted.

Here, the abnormal event refers to an event such as a sign of danger to the heart, abnormality of the heart, and the like and may be detected through an electrocardiogram digital signal or may be set through an input through an input unit. The tag related to the event may be generated considering an abnormal event acquired through the sensor unit 140 and context data related to the abnormal event. The tag related to the event may be generated by including information about pain associated with the heart on the basis of context data detected at the time point at which the abnormal event is detected. The tag related to the event may be generated on the basis of data (touch, voice, or the like) input through an input unit included in the electrocardiogram measuring apparatus 100. The tag may be set at a time when the data is input through the input unit. The tag may be set according to the strength, number of times, characteristics, and the like of the data input through the input unit. The tag related to the event may include input voice data, text data, image data, and the like. The tag related to the event may be set through an on/off button.

In another embodiment, the tag related to the event may be generated by including information about pain related to the heart, life discomfort, and the like on the basis of context data detected at the detected time point. The processor 130 may further collect context data in relation to the abnormal event. The processor 130 may sense context data through the sensor unit 140 or may receive context data through a user terminal 200. The context data may include a change in the movement of a user adjacent to the detection time point of the abnormal event, an input value through the input unit, input data input through the user terminal, and the like.

The processor 130 may separately generate, as data, intervals in which the abnormal event is included. The processor 130 may retrieve intervals into which a tag is inserted and separately generate tag measurement data obtained by collecting data about the intervals into which the tag is inserted. The processor 130 may transmit the tag measurement data to the user terminal 200 of a preset manager. Here, the manager may be a user having a preset medical-related authority (diagnosis, treatment, and the like) but is not limited thereto, and may be a person having various types of authority. The manager may be set in association with an object or the electrocardiogram measuring apparatus 100.

The processor 130 may further insert, into the tag measurement data, a message received from the user terminal 200. Also, when such a message or tag is inserted, different conversion gain than when such a message or tag is not inserted may be applied. When such a message or tag is inserted, measurement data of an electrocardiogram signal may be generated.

The sensor unit 140 may include movement sensor, acoustic sensor, and user input sensor. In a case of movement sensing. The sensor unit 140 may sense movements by detecting movements in X-axis, Y-axis, and Z-axis directions. Movement of an object may be sensed through the sensor unit 140. The sensor unit 140 may be implemented as a 3-axis or 6-axis sensor.

The power supply unit 150 supplies power to the signal detector 110, the signal converter 120, the memory 160, the processor 130, and the like. The power supply unit 150 may be a lithium iron phosphate (LiFePO4) battery but is not limited thereto and may be manufactured as a lithium cobalt oxide (LiCoO2) battery, a lithium titanate battery, or the like. The power supply unit 150 may be a rechargeable battery or a disposable battery.

Figure 6:
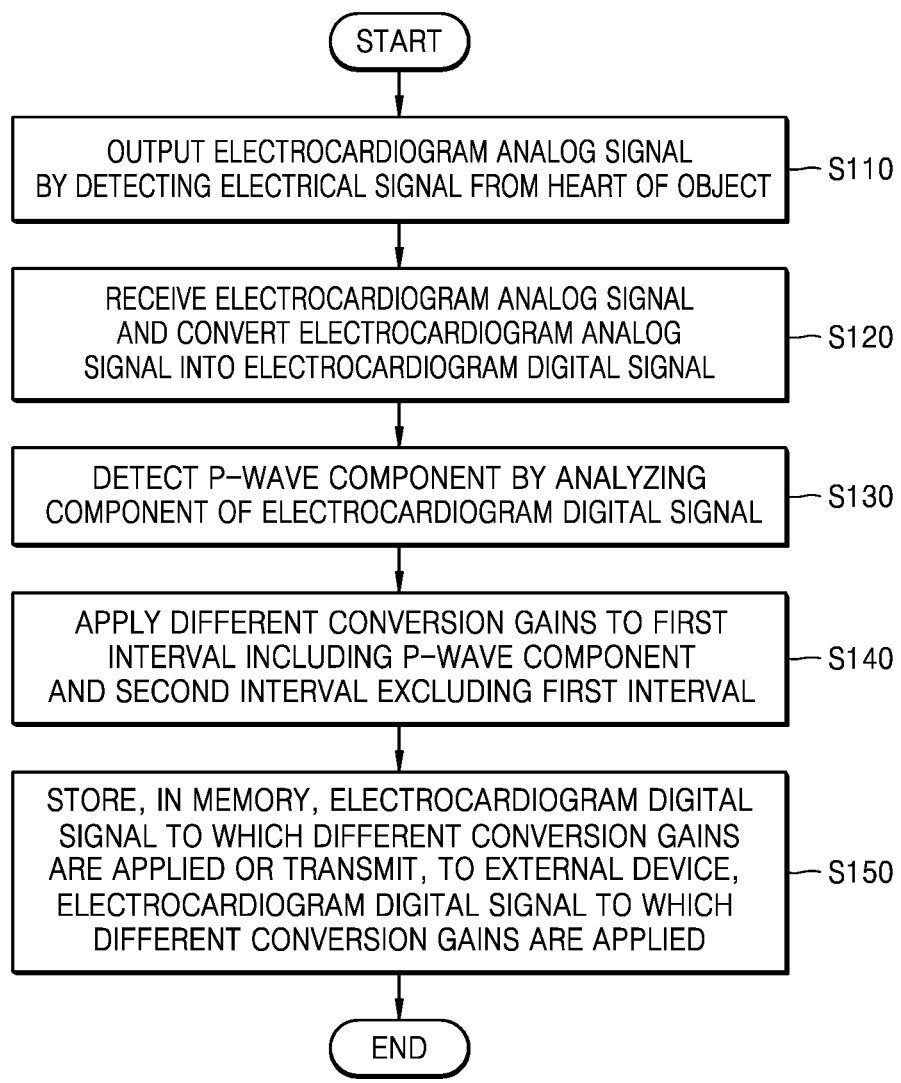
FIG. 6 is a flowchart of a method of measuring an electrocardiogram, according to one or more embodiments.
Figure 8:
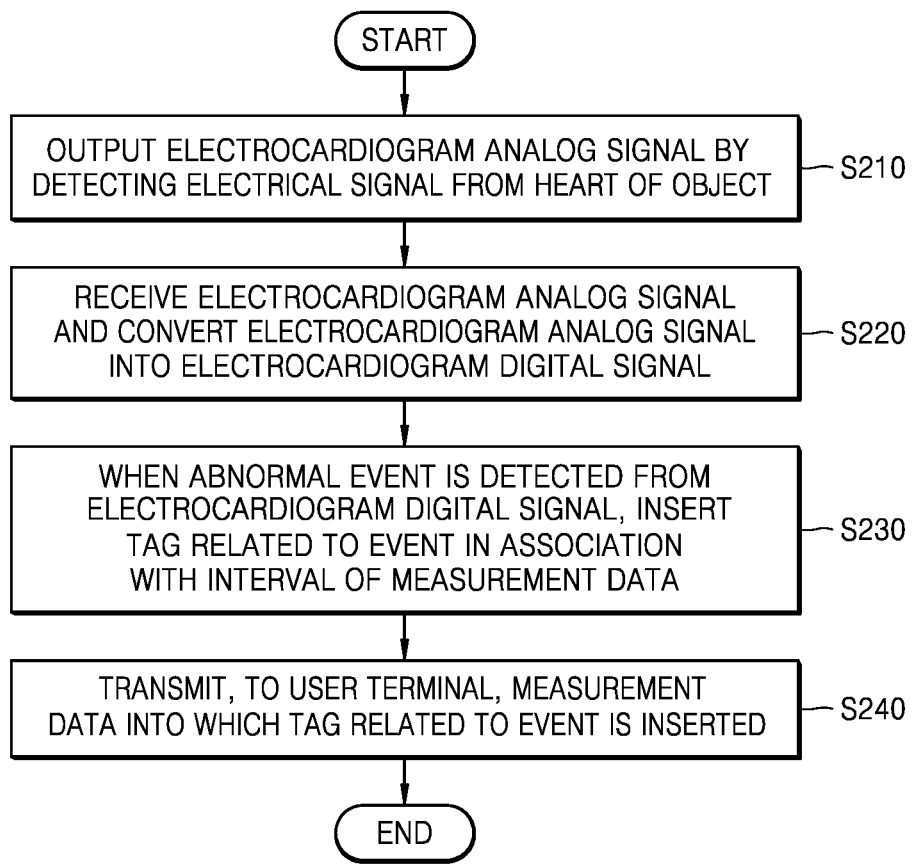
FIG. 8 is a flowchart of a method of measuring an electrocardiogram, according to one or more other embodiments.

The memory 160 may store data related to electrocardiogram measurement. The memory 160 may store information about an object, a measurement time, and data related to a measured electrocardiogram. The memory 160 may be hardware storing various types of data processed in the electrocardiogram measuring apparatus 100. The memory 160 may store pieces of data processed by the processor 130 and data to be processed by the processor 130, in particular, may store examples of conversion gains to be applied and conversion gains in respective operations as illustrated in FIG. 6. The memory 160 may store an event as illustrated in FIG. 8 and a tag related to the event. The memory 160 may be implemented as various types, such as random access memory (RAM) such as dynamic random access memory (DRAM) and static random access memory (SRAM), read-only memory (ROM), and electrically erasable programmable read-only memory (EEPROM).

The communicator 170 may receive a control signal from an external electronic device. The communicator 170 may transmit measured data to the external electronic device.

The electrocardiogram measuring apparatus 100 may include the signal processing unit 125 which detects a particular component by analyzing a signal and generate measurement data by applying a conversion gain on the basis of the particular component or the signal detector 110 or the signal converter 120 may detect a particular component by analyzing a signal and generate measurement data by applying a conversion gain on the basis of the particular component. A process of generating measurement data by the signal detector 110 or the signal converter 120 may be the same as the operation of the signal processing unit 125. In another embodiment, a process of generating measurement data may be performed by at least two of a signal detector, a signal converter, and a signal processing unit. FIG. 2 illustrates the signal processing unit 125 separately, but the signal processing unit 125 may be implemented with firmware in the processor 130.

Figure 3:
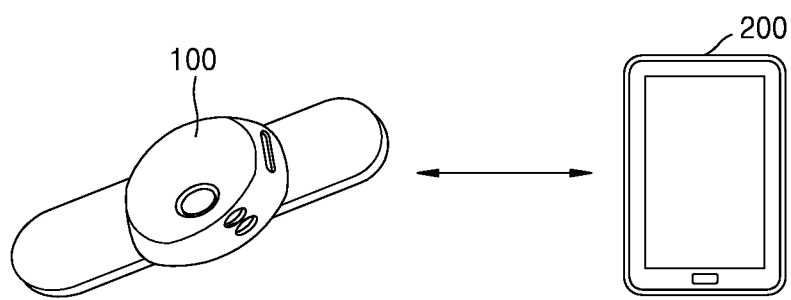
FIG. 3 is a view of a network environment connected to an apparatus for measuring an electrocardiogram.
Figure 4:
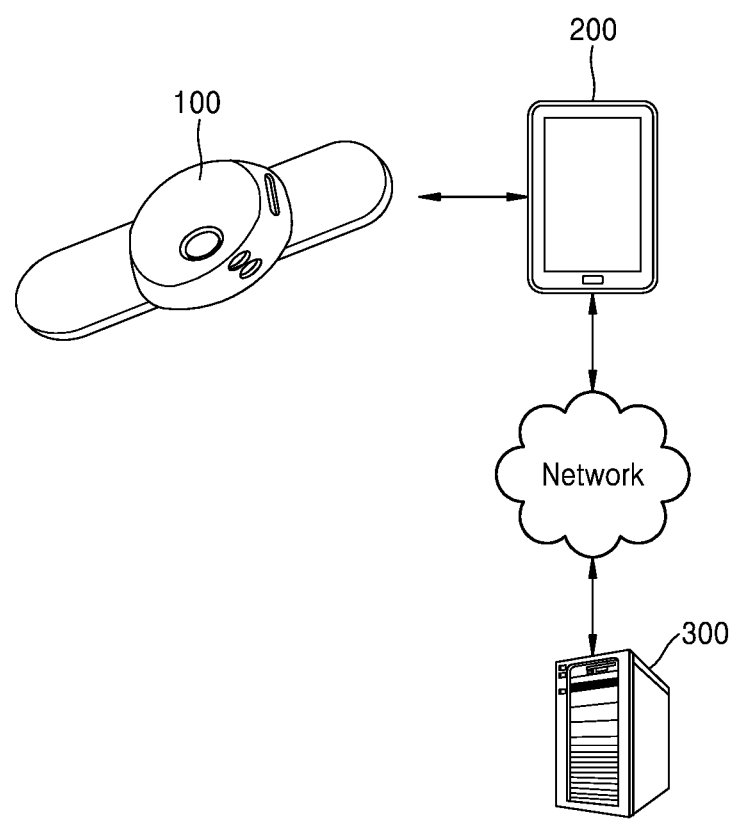
FIG. 4 illustrates another network environment connected to the apparatus for measuring an electrocardiogram.
Figure 5:
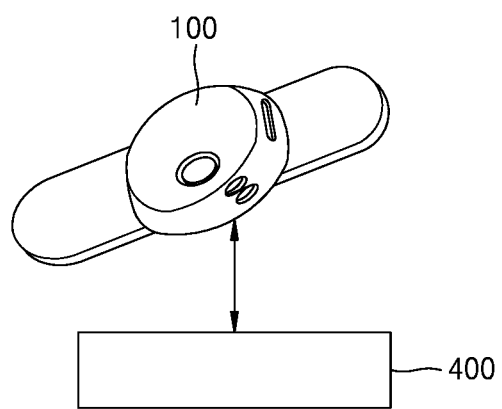
FIG. 5 illustrates further another network environment connected to the apparatus for measuring an electrocardiogram.

FIGS. 3 through 5 are views of a network environment connected to the electrocardiogram measuring apparatus 100.

As illustrated in FIG. 3, the electrocardiogram measuring apparatus 100 may operate while exchanging data with the user terminal 200. Here, the user terminal 200 may be used in a small electronic device such as a mobile phone, a smart phone, a laptop computer, a digital broadcasting terminal, a personal digital assistant (PDA), a portable multimedia player (PMP), navigation, an MP3 player, an electronic toothbrush, an electronic tag, a lighting device, a remote control, and a fishing boat, but is not limited thereto. The user terminal 200 may be a mobile device, and the term "terminal" or "device" may be used interchangeably.

The electrocardiogram measuring apparatus 100 may transmit a measured electrocardiogram signal to the user terminal 200. The electrocardiogram measuring apparatus 100 may store an electrocardiogram signal including a tag related to an abnormal event related to the heart and transmit the electrocardiogram signal including the tag to the user terminal 200. The electrocardiogram measuring apparatus 100 may transmit, to the user terminal 200, measurement data generated by linking an electrocardiogram signal to a change in movement detected through a sensor unit, an input obtained through an input unit (a voice input unit, a text input unit, a button input unit, an image input unite, or the like), and input data received through the user terminal 200. The electrocardiogram measuring apparatus 100 may collect measurement data of intervals in which an abnormal event occurs and corresponding time points and transmit the collected measurement data and time points to the user terminal 200.

The electrocardiogram measuring apparatus 100 may transmit a measured electrocardiogram according to a request from the user terminal 200. The electrocardiogram measuring apparatus 100 may transmit the measured electrocardiogram according to a preset period.

The electrocardiogram measuring apparatus 100 may be controlled according to a control signal from the user terminal 200. The electrocardiogram measuring apparatus 100 may start or end measuring an electrocardiogram signal according to a measurement start signal or a measurement end signal from the user terminal 200. The electrocardiogram measuring apparatus 100 may delete data recorded in a memory according to a data deletion signal from the user terminal 200.

The electrocardiogram measuring apparatus 100 may transmit information related to power to the user terminal 200. The electrocardiogram measuring apparatus 100 may transmit an alarm for the capacity of a power supply unit, whether or not the power supply unit is replaced, whether or not remaining power in the power supply unit is enough, and the like to be output through the user terminal 200. An alarm for notifying whether or not the electrocardiogram measuring apparatus 100 operates for a preset time may be also generated and transmitted to the user terminal 200. A time at which measurement is determined may be set through the user terminal 200 or may be set through an input unit in the electrocardiogram measuring apparatus 100, for example, may be set such as 24 hours, 48 hours, or the like.

The electrocardiogram measuring apparatus 100 may transmit information related to sensed movement to the user terminal 200. When the sensed movement is out of an excessive range or an electrocardiogram is not recorded, the electrocardiogram measuring apparatus 100 may transmit an alarm for this to the user terminal 200.

The user terminal 200 that communicates with the electrocardiogram measuring apparatus 100 may be registered through a preset registration process, and a single user terminal 200 or a plurality of user terminals 200 may be provided. As illustrated in FIG. 4, the electrocardiogram measuring apparatus 100 may operate while exchanging data with the user terminal 200 or an electrocardiogram management server 300.

The electrocardiogram management server 300 may manage electrocardiogram measurement data received from a plurality of electrocardiogram measuring apparatuses 100 and may use data of the electrocardiogram measuring apparatuses 100. The electrocardiogram measurement data may include an electrocardiogram signal itself and processed electrocardiogram data by measuring apparatus 100. Also, the electrocardiogram measurement data may include only electrocardiogram data of an interval in which an abnormal event occurs. The electrocardiogram management server 300 may use data from the electrocardiogram measuring apparatus 100, which and may include information about a time when an electrocardiogram is measured, accumulated time information, information about a time when the electrocardiogram is not measured, information about a time when an abnormal event occurs, and the like.

The electrocardiogram management server 300 may manage electrocardiogram data from the electrocardiogram measuring apparatus 100 in association with an object. The electrocardiogram management server 300 may store electrocardiogram data for a first object in association with the first object. The electrocardiogram management server 300 manages an electrocardiogram signal of an object. The electrocardiogram management server 300 may manage a conversion gain applied to the electrocardiogram signal and information about an interval in which the electrocardiogram signal is converted. The electrocardiogram management server 300 may manage information about a particular component for determining a converted interval, information about determination logic for the particular component, measurement data generation logic, and the like. The electrocardiogram management server 300 may distribute collected electrocardiogram signals. The electrocardiogram management server 300 may be designed to provide data of the first object to a user having authority over the first object. The user having authority over the first object may be at least one of a medical worker, a legal officer, and a person employed for management. The electrocardiogram management server 300 may transmit electrocardiogram data of an object requested by a request of the medical worker.

The electrocardiogram management server 300 may further receive context data from the electrocardiogram measuring apparatus 100. The electrocardiogram management server 300 may generate an analysis report by analyzing data received from the electrocardiogram measuring apparatus 100. The analysis report may include an event acquired through an electrocardiogram. The event may include an event related to movement of the heart, an event recorded by a user, an event recorded in a voice recognition method, movement and exercise amount of the user, a temperature value of a device, the heart rate, and the like. The analysis report may include data about an abnormal symptom of the heart. The analysis report may store, as separate data, a time point at which an abnormal symptom felt in the heart occurs, an electrocardiogram at the time point of the occurrence, and the like by using a tag related to an abnormal event and the like.

The electrocardiogram management server 300 may receive measurement data of the electrocardiogram measuring apparatus 100 through the user terminal 200.

As illustrated in FIG. 5, the electrocardiogram measuring apparatus 100 may be supplied with power through an external charging device 400. The external charging device 400 may charge the electrocardiogram measuring apparatus 100 by flowing a current through electromagnetic induction. The external charging device 400 may be configured in a pad shape, a cradle shape, an access point (AP) shape, a small base station shape, a stand shape, a ceiling-buried shape, a wall-hanging shape, or the like. One external charging device 400 may transmit power to a plurality of electrocardiogram measuring apparatuses 100 in a wireless or wired manner. The external charging device 400 may be implemented to check a power state of the electrocardiogram measuring apparatus 100 to automatically stop charging when the capacity of power is charged.

State information indicating whether or not the electrocardiogram measuring apparatus 100 is charged may be output through the electrocardiogram measuring apparatus 100 or the user terminal 200. When the electrocardiogram measuring apparatus 100 is completely charged, a notification or alert may be generated through the electrocardiogram measuring apparatus 100 or the user terminal 200.

When a power level of the power supply unit is less than or equal to a preset first minimum value, the electrocardiogram measuring apparatus 100 may use power only to measure and store an electrocardiogram and may not use power to transmit data or the like to another device.

When the power level of the power supply unit is less than or equal to a preset second minimum value, the electrocardiogram measuring apparatus 100 may adjust a period for measuring and storing an electrocardiogram longer.

FIG. 6 is a flowchart of a method of measuring an electrocardiogram, according to one or more embodiments.

As illustrated in FIG. 6, in operation S110, the electrocardiogram measuring apparatus 100 may output an electrocardiogram analog signal by detecting an electrical signal from the heart of an object.

In operation S120, the electrocardiogram measuring apparatus 100 may convert the electrocardiogram analog signal into an electrocardiogram digital signal.

In operation S130, the electrocardiogram measuring apparatus 100 may detect a particular component such as a P-wave component or the like by analyzing a component of the electrocardiogram digital signal. In an alternative embodiment, the electrocardiogram measuring apparatus 100 may detect a P-wave component from the electrocardiogram digital signal by using the magnitude and slope of a signal. An average magnitude or an average slope of the P-wave component may be detected on the basis of collected data about P-wave components, and the P-wave component may be detected through the collected data about the P-wave components.

In another embodiment, the electrocardiogram measuring apparatus 100 may detect a P-wave component by comparing an electrocardiogram digital signal with a template (form) of a standard electrocardiogram waveform.

In another embodiment, the electrocardiogram measuring apparatus 100 may detect a peak component from an electrocardiogram signal by using the magnitude and slope of a signal and detect a P-wave component by using the peak component. The electrocardiogram measuring apparatus 100 may detect, as a P-wave component, a component which occurs closest to a peak component and at which the magnitude of a signal is not 0, from a random interval before the peak component.

In relation to detection of a peak component, the electrocardiogram measuring apparatus 100 may detect, as a peak component, a time point at which a slope of a signal is changed from a positive (+) value to a negative (−) value, a time point at which the magnitude of a signal reaches a maximum value, or the like. The electrocardiogram measuring apparatus 100 may detect, as a P-wave component, an interval in which the magnitude of a signal is within a preset range, from an interval before a peak component. The electrocardiogram measuring apparatus 100 may detect, as a P-wave component, an interval which is closest to a peak component and in which the magnitude of a signal is not 0, from an interval before the peak component. The electrocardiogram measuring apparatus 100 may detect, as a P-wave component, an interval in which a shape of an electrocardiogram signal generated closest to a peak component is similar to a preset pattern, from an interval before a peak component.

The electrocardiogram measuring apparatus 100 may generate measurement data for an electrocardiogram signal by applying a first conversion gain to a signal in a first interval including a P-wave component and applying a second conversion gain to a signal in a remaining interval excluding the first interval. Here, the second conversion gain may be a value less than the first conversion gain. In other words, detection, visual display, recognition, and the like of a P-wave component may be enhanced by applying, to the P-wave component, a conversion gain greater than a conversion gain applied to a remaining interval.

Here, the first conversion gain applied to the P-wave component may increase or decrease throughout several stages. When the magnitude of the P-wave component does not satisfy preset conditions after the first conversion gain is applied, the first conversion gain may be adjusted to another value. For example, when the magnitude of the P-wave component is less than or equal to a minimum magnitude value after the first conversion gain is applied, the first conversion gain may be adjusted to a value greater than previous conversion gain. Also, when the magnitude of the P-wave component is greater than or equal to a maximum magnitude value after the first conversion gain is applied, the first conversion gain may be adjusted to a value less than the previous conversion gain. The range of adjustment of conversion gain may be determined according to a preset ratio.

The electrocardiogram measuring apparatus 100 may set, as an interval including a P-wave component, points at which a slope value or an absolute value of the slope value is less than or equal to a preset value and the magnitude of a signal is not 0, from an interval before a peak component.

In operation S140, the electrocardiogram measuring apparatus 100 may apply different conversion gains to a first interval including a P-wave component and a second interval that is a remaining interval excluding the first interval.

The processor 130 of the electrocardiogram measuring apparatus 100 may store, in a memory, applied conversion gains along with measurement data for an electrocardiogram or transmit, to an external electronic device, the applied conversion gains along with the measurement data for the electrocardiogram. An additional table including applied conversion gains may be generated.

In operation S150, the electrocardiogram measuring apparatus 100 may store, in a memory, an electrocardiogram digital signal to which different conversion gains are applied for respective intervals and transmit the electrocardiogram digital signal to an external device.

Figure 7:
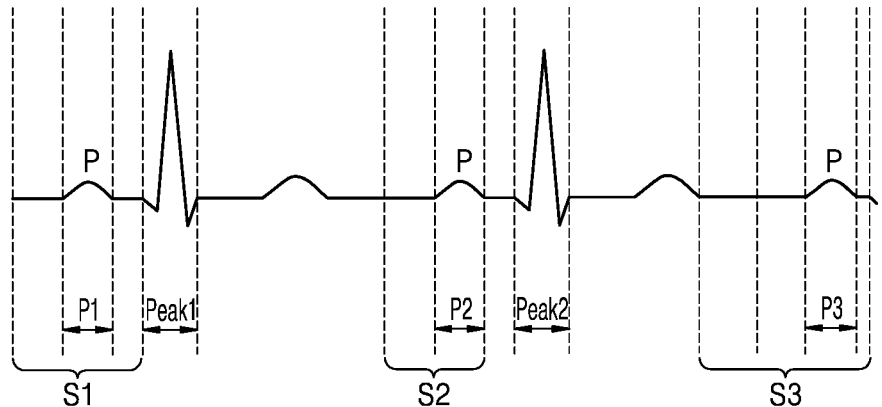
FIG. 7 is an example view related to setting of a first interval and a second interval.

FIG. 7 is an example view related to setting of a first interval and a second interval.

The electrocardiogram measuring apparatus 100 may set an interval including a P-wave component to a random interval preceding a peak component. A P-wave component may be detected from the interval preceding the peak component on the basis of the magnitude, a slope, and the like of a signal. The electrocardiogram measuring apparatus 100 may set first intervals S1 and S3 including an interval in which the magnitude of a signal adjacent to a P-wave component is zero(0). The electrocardiogram measuring apparatus 100 may set a first interval S2 including an interval in which the magnitude of an adjacent signal before a P-wave component is zero(0). This zero (0) helps to reduce data size and to control operation of the electrocardiogram measuring apparatus 100.

FIG. 8 is a flowchart of a method of measuring an electrocardiogram, according to one or more embodiments.

As illustrated in FIG. 8, in operation S210, the electrocardiogram measuring apparatus 100 may output an electrocardiogram analog signal by detecting an electrical signal from the heart of an object.

In operation S220, the electrocardiogram measuring apparatus 100 may convert the electrocardiogram analog signal into an electrocardiogram digital signal.

In operation S230, when an abnormal event is detected from the electrocardiogram digital signal, the electrocardiogram measuring apparatus 100 detects a time point at which the abnormal event is detected and a corresponding interval of measurement data and insert a tag related to an event in association with the interval of the measurement data.

The electrocardiogram measuring apparatus 100 generates the measurement data on the basis of the electrocardiogram digital signal and stores the measurement data in a memory. When an abnormal event is detected from the electrocardiogram digital signal, the electrocardiogram measuring apparatus 100 may detect a time point at which the abnormal event is detected and a corresponding interval of measurement data, insert a tag related to an event in association with the interval of the measurement data, and transmit, to an external user terminal, the measurement data into which the tag is inserted.

The tag related to the event may be generated by including information about pain related to the heart on the basis of context data detected at a time point at which the abnormal event is detected. The tag related to the event may be generated on the basis of data input through an input unit included in the electrocardiogram measuring apparatus 100. The tag related to the event may include input voice data, text data, image data, and the like. The tag related to the event may be set through an on/off button.

In another embodiment, the tag related to the event may be generated by including information about pain related to the heart, life discomfort, and the like on the basis of context data detected at a time point at which the abnormal event is detected. The electrocardiogram measuring apparatus 100 may further collect context data in relation to the abnormal event. The electrocardiogram measuring apparatus 100 may sense context data through a sensor unit or may receive context data through a user terminal. Context data may include a change in movement adjacent to a detection time point of an abnormal event, an input value through an input unit adjacent to the event detection time point, input data input through a user terminal adjacent to the event detection time point, and the like.

In operation S240, the electrocardiogram measuring apparatus 100 transmits, to a user terminal, the measurement data into which the tag related to the event is inserted.

Therefore, the electrocardiogram measuring apparatus 100 may measure an electrocardiogram and simultaneously generate measurement data including an abnormal event occurring in heart activity and a tag related to an event.

FIGS. 9 through 11 are flowcharts of a method of measuring an electrocardiogram, according to various embodiments.

In operation S310, the signal detector 110 of the electrocardiogram measuring apparatus 100 outputs an electrocardiogram analog signal by detecting an electrical signal from the heart of an object.

In operation S320, the signal converter 120 of the electrocardiogram measuring apparatus 100 may receive the electrocardiogram analog signal, convert the electrocardiogram analog signal into an electrocardiogram digital signal, detect a particular interval, for example, a component of a P-wave interval by analyzing components of the electrocardiogram digital signal, and apply different conversion gains to a signal in the particular interval and a signal in a remaining interval excluding the particular interval.

In operation S330, the processor 130 of the electrocardiogram measuring apparatus 100 may store, in a memory, the electrocardiogram digital signal to which the different conversion gains are applied for respective intervals or transmit the electrocardiogram digital signal to the outside. Here, the processor 130 may convert the electrocardiogram digital signal into measurement data according to a preset rule and store the measurement data in the memory or transmit the measurement data to the outside.

As illustrated in FIG. 10, in operation S410, the signal detector 110 of the electrocardiogram measuring apparatus 100 may generate an electrocardiogram analog signal by detecting an electrical signal from the heart of an object, detect a particular component by analyzing components of the electrocardiogram analog signal, detect an interval corresponding to the particular interval, and convert the electrocardiogram analog signal by applying different conversion gains to a signal in the interval and a signal in a remaining interval excluding the interval.

In operation S420, the signal converter 120 of the electrocardiogram measuring apparatus 100 receives the electrocardiogram analog signal and converts the electrocardiogram analog signal into an electrocardiogram digital signal.

In operation S430, the processor 130 of the electrocardiogram measuring apparatus 100 records the electrocardiogram digital signal in a memory or transmit the electrocardiogram digital signal to an external electronic device. Here, the processor 130 may convert the electrocardiogram digital signal into measurement data according to a preset rule and may store the measurement data in the memory or may transmit the measurement data to the external electronic device.

As illustrated in FIG. 11, in operation S510, the signal detector 110 of the electrocardiogram measuring apparatus 100 generates an electrocardiogram analog signal by detecting an electrical signal from the heart of an object, detects a particular component by analyzing components of the electrocardiogram analog signal, and detects an interval corresponding to the particular component.

In operation S520, the signal converter 120 of the electrocardiogram measuring apparatus 100 receives the electrocardiogram analog signal, converts the electrocardiogram analog signal into an electrocardiogram digital signal, and converts the electrocardiogram digital signal by applying different conversion gains to a signal in the interval and a signal in a remaining interval excluding the interval.

In operation 530, the processor 130 of the electrocardiogram measuring apparatus 100 records the electrocardiogram digital signal in a memory or transmits the electrocardiogram digital signal to an external electronic device. Here, the processor 130 may convert the electrocardiogram digital signal into measurement data according to a preset rule and may store the measurement data in the memory or may transmit the measurement data to the external electronic device.

The apparatus described above may be implemented with hardware components, software components, and/or combinations of hardware components and software components. For example, the apparatus and components described in one or more embodiments may be implemented, for example, by using one or more general-purpose computers or special-purpose computers such as a processor, a controller, an arithmetic logic unit (ALU), a digital signal processor, a microcomputer, a field programmable gate array (FPGA), a programmable logic unit (PLU), a microprocessor, or any other devices capable of executing and responding to instructions. A processing unit may perform an operating system (OS) and one or more software applications executed on the OS. Also, the processing unit may access, store, control, process, and generate data in response to execution of software. For convenience of understanding, while one processing unit has been described as being used, it will be understood by one of ordinary skill in the art that the processing unit may include a plurality of processing elements and/or a plurality of types of processing elements. For example, the processing unit may include a plurality of processors or one processor and one controller. Also, the processing unit may include another processing configuration such as a parallel processor.

Software may include a computer program, code, instructions, or a combination of one or more thereof and may configure the processing unit to operate as wanted or instruct the processing unit independently or collectively. Software and/or data may be permanently or temporarily embodied in any type of machine, component, physical device, virtual equipment, computer storage medium or device, or transmitted signal wave to be interpreted by the processing unit or to provide the processing unit with instructions or data. Software may be distributed over networked computer systems and may be stored or executed in a distributed manner. Software and/or data may be stored on one or more computer-readable recording media.

The method according to one or more embodiments may be implemented in the form of a computer instruction that may be executed through various types of computer units and recorded on a computer-readable recording medium. The computer-readable recording medium may include program instructions, data files, data structures, or the like alone or in combination. The program instructions recorded on the medium may be specially designed and configured for an embodiment or may be known and available to one of ordinary skill in computer software. Examples of the computer-readable recording medium include magnetic media such as hard disks, floppy disks, and magnetic tapes, optical media such as CD-ROM and DVD, magneto-optical media such as floptical disks, and hardware devices specially configured to store and perform program instructions such as ROM, RAM, and flash memory. Examples of the program instructions include high-level language code that may be executed by a computer using an interpreter or the like, as well as machine language code made by a compiler. The hardware device described above may be configured to operate as one or more software modules to perform operations of the embodiments, and the reverse is the same.

According to one or more embodiments, the interpretation of a small-sized signal included in an electrocardiogram signal may be enhanced by applying different conversion grains to the electrocardiogram signal for respective intervals.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. An electrocardiogram measuring apparatus comprising:
   a mounting part made of a flexible material that is deformed to fit a curved surface of a surface of a human body;
   a case comprising a button arranged on a top surface thereof and operable to receive an input from a user, the case configured to house:
     a signal detector outputting an electrocardiogram analog signal by detecting an electrical signal from a heart of an object;
     a signal converter receiving the electrocardiogram analog signal from the signal detector and converting the electrocardiogram analog signal into an electrocardiogram digital signal;
     a processor receiving and recording, in a memory, the electrocardiogram digital signal, the processor further comprising a signal processing unit detecting a particular component among the electrocardiogram digital signal,
       wherein the signal processing unit is configured to:
         detect a first interval including the particular component
         apply two or more different conversion gains to a first electrocardiogram digital signal in the first interval and a second electrocardiogram digital signal in a remaining interval excluding the first interval;

generate first measurement data corresponding to the first electrocardiogram digital signal after applying the two or more different conversion gains, wherein the first measurement data includes an enhanced particular component; and generate second measurement data corresponding to the second electrocardiogram digital signal after applying the two or more different conversion gains;

wherein the processor is further configured to transmit the first measurement data and the second measurement data to an external electronic device; and a power supply unit supplying power to the signal detector, the signal converter, the signal processing unit, the memory, and the processor.

2. The electrocardiogram measuring apparatus of claim 1, wherein the signal processing unit is further configured to:
detect a P-wave component from the electrocardiogram digital signal by using a magnitude and a slope of the electrocardiogram digital signal.

3. The electrocardiogram measuring apparatus of claim 2, wherein the signal processing unit detects, from the electrocardiogram digital signal, the P-wave component by using a peak component including a point at which a largest magnitude of the electrocardiogram digital signal occurs within an interval of the electrocardiogram digital signal,
wherein the interval is determined by a heart movement of the human body; and
wherein the signal processing unit detects the P-wave component occurring closest to the peak component in the first interval preceding or following the peak component for a first time.

4. The electrocardiogram measuring apparatus of claim 3, wherein the signal processing unit is further configured to detect a set of points which is adjacent to the peak component and at which a slope is not zero, wherein the set of points is associated with the first interval including the P-wave component.

5. The electrocardiogram measuring apparatus of claim 1, wherein the two or more different conversion gains comprise a first conversion gain and a second conversion again, and the signal processing unit is further configured to apply:
the first conversion gain to the first electrocardiogram digital signal; and
the second conversion gain to the second electrocardiogram digital signal.

6. The electrocardiogram measuring apparatus of claim 5, wherein the first conversion gain is greater than the second conversion gain such that a magnitude of the P-wave component of the first electrocardiogram digital signal is increased.

7. The electrocardiogram measuring apparatus of claim 6, wherein the second conversion gain is set to zero in the remaining interval excluding the first interval.

8. The electrocardiogram measuring apparatus of claim 1, wherein the signal processing unit is further configured to:

detect a P-wave component by comparing the electrocardiogram digital signal with a template of a standard electrocardiogram waveform.

9. The electrocardiogram measuring apparatus of claim 1, wherein the signal converter is further configured to control magnitudes of the two or more conversion gains.

10. An electrocardiogram measuring method comprising:
mounting the electrocardiogram measuring apparatus of claim 1 on a location proximate a heart of an object;
obtaining an electrocardiogram analog signal from the heart of the object;
converting the electrocardiogram analog signal into an electrocardiogram digital signal;
storing, in a memory, the electrocardiogram digital signal;
detecting a P-wave component among the electrocardiogram digital signal;
detecting a first interval corresponding to the P-wave component;
applying two or more different conversion gains to a first electrocardiogram digital signal in the first interval and a second electrocardiogram digital signal in a remaining interval excluding the first interval, respectively;
generating first measurement data for the first electrocardiogram digital signal, wherein the first measurement data includes an enhanced P-wave component;
generating second measurement data for the second electrocardiogram digital signal; and
transmitting, to an external electronic device, the first and the second measurement data.

11. The electrocardiogram measuring method of claim 10, wherein the step of detecting the P-wave component further comprises:
detecting the P-wave component from the electrocardiogram digital signal by using a magnitude and a slope of a signal.

12. The electrocardiogram measuring method of claim 10, wherein the step of detecting the P-wave component further comprises:
detecting the P-wave component by comparing the electrocardiogram digital signal with a template of a standard electrocardiogram waveform.

13. The electrocardiogram measuring method of claim 10, wherein the step of detecting the P-wave component further comprises:
detecting, from the electrocardiogram digital signal, the P-wave component by using a peak component including a point at which a largest magnitude of the electrocardiogram digital signal occurs within an interval of the electrocardiogram digital signal,
wherein the interval is determined by a heart movement of a human body; and
wherein detecting the P-wave component further comprises detecting the P-wave component occurring closest to the peak component in the first interval preceding or following the peak component for a first time.

14. The electrocardiogram measuring method of claim 13, further comprising detecting a set of points which is adjacent to the peak component and at which a slope is not zero, wherein the set of points is associated with the first interval including the P-wave component.

* * * * *